United States Patent
Zhang et al.

(10) Patent No.: US 6,511,986 B2
(45) Date of Patent: Jan. 28, 2003

(54) METHOD OF TREATING ESTROGEN RECEPTOR POSITIVE CARCINOMA

(75) Inventors: Yixian Zhang, Nanuet, NY (US); Tammy M. Sadler, Chester, NY (US); Philip Frost, Morris Township, NJ (US); Lee Martin Greenberger, Montclair, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/923,217

(22) Filed: Aug. 6, 2001

(65) Prior Publication Data

US 2002/0045638 A1 Apr. 18, 2002

Related U.S. Application Data

(60) Provisional application No. 60/224,326, filed on Aug. 11, 2000.

(51) Int. Cl.$^7$ .............................................. A61K 31/44
(52) U.S. Cl. ................. 514/280; 514/183; 514/217.08; 514/291; 514/330; 514/331; 514/874; 514/922
(58) Field of Search ................................. 514/280, 291, 514/330, 874, 331, 922, 183, 217.08

(56) References Cited

U.S. PATENT DOCUMENTS

| | | | |
|---|---|---|---|
| 4,316,885 A | 2/1982 | Rakhit | |
| 4,650,803 A | 3/1987 | Stella et al. | |
| 5,023,263 A | 6/1991 | Von Burg | |
| 5,023,264 A | 6/1991 | Caufield et al. | |
| 5,100,883 A | 3/1992 | Schiehser | |
| 5,118,677 A | 6/1992 | Caufield | |
| 5,118,678 A | 6/1992 | Kao et al. | |
| 5,120,842 A | 6/1992 | Failli et al. | |
| 5,130,307 A | 7/1992 | Failli et al. | |
| 5,151,413 A | 9/1992 | Caufield et al. | |
| 5,162,333 A | 11/1992 | Failli et al. | |
| 5,177,203 A | 1/1993 | Failli et al. | |
| 5,221,670 A | 6/1993 | Caufield | |
| 5,233,036 A | 8/1993 | Hughes | |
| 5,256,790 A | 10/1993 | Nelson | |
| 5,258,389 A | 11/1993 | Goulet et al. | |
| 5,260,300 A | 11/1993 | Hu | |
| 5,262,423 A | 11/1993 | Kao | |
| 5,302,584 A | 4/1994 | Kao et al. | |
| 5,362,718 A | 11/1994 | Skotnicki et al. | |
| 5,373,014 A | 12/1994 | Failli et al. | |
| 5,378,836 A | 1/1995 | Kao et al. | |
| 5,385,908 A | 1/1995 | Nelson et al. | |
| 5,385,909 A | 1/1995 | Nelson et al. | |
| 5,385,910 A | 1/1995 | Ocalin | |
| 5,389,639 A | 2/1995 | Failli | |
| 5,391,730 A | 2/1995 | Skotnicki | |
| 5,411,967 A | 5/1995 | Kao et al. | |
| 5,434,260 A | 7/1995 | Skotnicki et al. | |
| 5,463,048 A | 10/1995 | Skotnicki et al. | |
| 5,480,988 A | 1/1996 | Failli et al. | |
| 5,480,989 A | 1/1996 | Kao et al. | |
| 5,489,680 A | 2/1996 | Failli et al. | |
| 5,491,231 A | 2/1996 | Nelson et al. | |
| 5,504,091 A | 4/1996 | Molnar-Kimber et al. | |
| 5,563,145 A | 10/1996 | Failli et al. | |
| 5,665,772 A | 9/1997 | Cottens et al. | |
| 5,780,462 A | 7/1998 | Lee et al. | |
| 5,998,402 A | 12/1999 | Miller et al. | |

FOREIGN PATENT DOCUMENTS

| | | |
|---|---|---|
| WO | WO97 48397 | 12/1997 |
| WO | WO99 63974 | 12/1999 |

Primary Examiner—Frederick Krass
(74) Attorney, Agent, or Firm—Arnold S. Milowsky

(57) ABSTRACT

This invention provides a method of treating or inhibiting an estrogen receptor positive carcinoma in a mammal in need thereof, which comprises providing said mammal with an effective amount of a combination of a rapamycin and an antiestrogen.

16 Claims, No Drawings

METHOD OF TREATING ESTROGEN RECEPTOR POSITIVE CARCINOMA

This application claims priority form copending provisional application Ser. No. 60/224,326, filed Aug. 11, 2000, the entire disclosure of which is hereby incorporated by reference.

BACKGROUND OF THE INVENTION

This invention relates the use of a combination of a rapamycin and an antiestrogen in the treatment or inhibition of estrogen receptor positive carcinoma, particularly breast and ovarian cancer.

Breast cancer is a leading cause of female cancer deaths in the world. The growth of some human breast cancer cells is under hormonal control. Substantial evidence suggests that estrogen promotes the development of breast cancer. The biological effect of estrogen in the breast is mediated by estrogen receptor (ER), which is a member of a large family of ligand-inducible transcription factors. Upon binding to its receptor, the ligand initiates the dissociation of heat shock proteins from the receptor, receptor dimerization, phosphorylation, and binding to DNA response elements of target genes. After binding to DNA, ER differentially regulates transcription of target genes with or without other transcription factors and coactivators/corepressors. Estrogen action can be partially blocked by antagonists (antiestrogens) which act through ER in a way that is competitive with estrogen but fails to activate genes that promote cell growth. The antiestrogen tamoxifen (Tam) has been the first-line therapy in the treatment and management of breast cancer based on the estrogen responsiveness for stimulation of tumor growth. Unfortunately, the effectiveness of Tam therapy is hampered by its agonist activity in other tissues such as the uterus and side effects like hot flashes. There is a need to develop new antiestrogens or to develop optimal combinations of antiestrogens with other therapeutic agents to achieve better efficacy and reduce side effects.

Rapamycin is a macrocyclic triene antibiotic produced by *Streptomyces hygroscopicus,* which was found to have antifungal activity, particularly against *Candida albicans,* both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. Nos. 3,929,992; and 3,993,749]. Additionally, rapamycin alone (U.S. Pat. No. 4,885,171) or in combination with picibanil (U.S. Pat. No. 4,401,653) has been shown to have antitumor activity.

A rapamycin ester, rapamycin 42-ester with 3-hydroxy-2-(hydroxymethyl)-2-methylpropionic acid [disclosed in U.S. Pat. No. 5,362,718], also known as CCI-779, has been shown to have antitumor activity against a variety of tumor cell lines, in in vivo animal tumor models, and in Phase I clinical trials. [Gibbons, J., Proc. Am. Assoc. Can. Res. 40: 301 (1999); Geoerger, B., Proc. Am. Assoc. Can. Res. 40: 603 (1999); Alexandre, J., Proc. Am. Assoc. Can. Res. 40: 613 (1999); and Alexandre, J., Clin. Cancer. Res. 5 (November Supp.): Abstr. 7 (1999)].

Non-uterotrophic antiestrogens have been reported to have antitumor activity [see, U.S. Pat. No. 5,998,402]. 2-(4-Hydroxy-phenyl)-3-methyl-1-[4-(2-piperdin-1-yl-ethoxy)-benzyl-1H-indol-5-ol, also known as ERA-923, has been reported as being developed for the treatment of estrogen receptor positive metastatic breast cancer. [Gandhi T., 2000 ASCO Program/Proceedings, Abstract 875, (May 2000)].

DESCRIPTION OF THE INVENTION

This invention provides a method of treating or inhibiting estrogen receptor positive carcinoma in a mammal in need thereof, which comprises providing an effective amount of a combination of a rapamycin and an antiestrogen to said mammal.

As defined herein, the term "a rapamycin" defines a class of immunosuppressive compounds which contain the basic rapamycin nucleus (shown below). The rapamycins of this invention include compounds which may be chemically or biologically modified as derivatives of the rapamycin nucleus, while still retaining immunosuppressive properties. Accordingly, the term "a rapamycin" includes esters, ethers, oximes, hydrazones, and hydroxylamines of rapamycin, as well as rapamycins in which functional groups on the rapamycin nucleus have been modified, for example through reduction or oxidation. The term "a rapamycin" also includes pharmaceutically acceptable salts of rapamycins, which are capable of forming such salts, either by virtue of containing an acidic or basic moiety.

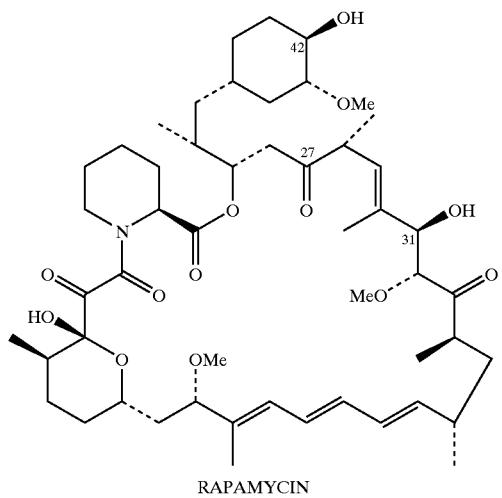

RAPAMYCIN

It is preferred that the esters and ethers of rapamycin are of the hydroxyl groups at the 42- and/or 31-positions of the rapamycin nucleus, esters and ethers of a hydroxyl group at the 27-position (following chemical reduction of the 27-ketone), and that the oximes, hydrazones, and hydroxylamines are of a ketone at the 42-position (following oxidation of the 42-hydroxyl group) and of 27-ketone of the rapamycin nucleus.

Preferred 42- and/or 31-esters and ethers of rapamycin are disclosed in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl ethers (U.S. Pat. No. 5,120,842); aminoesters (U.S. Pat. No. 5,130,307); acetals (U.S. Pat. No. 5,51,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909);

gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988);, carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462). The preparation of these esters and ethers are disclosed in the patents listed above.

Preferred 27-esters and ethers of rapamycin are disclosed in U.S. Pat. No. 5,256,790, which is hereby incorporated by reference. The preparation of these esters and ethers are disclosed in the patents listed above.

Preferred oximes, hydrazones, and hydroxylamines of rapamycin are disclosed in U.S. Pat. Nos. 5,373,014, 5,378,836, 5,023,264, and 5,563,145, which are hereby incorporated by reference. The preparation of these oximes, hydrazones, and hydroxylamines are disclosed in the above listed patents. The preparation of 42-oxorapamycin is disclosed in 5,023,263, which is hereby incorporated by reference.

Particularly preferred rapamycins include rapamycin [U.S. Pat. No. 3,929,9921], rapamycin 42-ester with 3-hydroxy-2-(hydroxymethyl)-2-methylpropionic acid [U.S. Pat. No. 5,362,718], and 42-O-(2-hydroxy)ethyl rapamycin [U.S. Pat. No. 5,665,772].

As used in accordance with this invention, the term antiestrogen is defined as a compound that will blunt or block the effects of an estrogen agonist, such as 17β-estradiol, when administered concomitantly in a test system. The term non-uterotrophic means antiestrogens which typically will not produce clinically significant endometrial proliferation.

Preferred antiestrogens include compounds such as triphenylene antiestrogens including tamoxifen and 4-hydroxytamoxifen; clomiphene; and non-uterotrophic antiesestrogens, such as those shown below in formulas I and II, raloxifene, droloxifene, idoxifine, nafoxidine, toremifene, TAT-59, levomeloxifene, LY-353381, CP-336156, MDL-103323, EM-800, and ICI-182,780.

Preferred non-uterotrophic antiestrtogens include compounds of formulas I or II having the structures

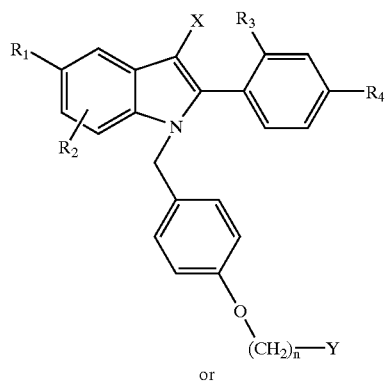

or

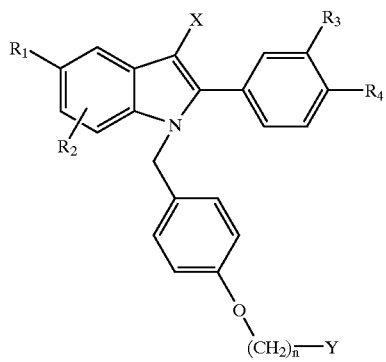

wherein:

$R_1$ is H, OH, carboalkoxy of 2–12 carbon atoms, alkoxy of 1–12 carbon atoms, halogen or mono- or polyfluoroalkoxy of 1–12 carbon atoms;

$R_2$ is H, OH, carboalkoxy of 2–12 carbon atoms, alkoxy of 1–12 carbon atoms, halogen, mono- or polyfluoroalkoxy of 1–12 carbon atoms, cyano, alkyl fo 1–6 carbon atoms, or trifluoromethyl, with the proviso that, when $R_1$ is H, $R_2$ is not OH.

$R_3$ and $R_4$ are each, independently, H, OH, carboalkoxy of 2–12 carbon atoms, alkoxy of 1–12 carbon atoms, halogen, mono- or poly-fluoroalkoxy of 1–12 carbon atoms, or cyano, with the proviso that, when $R_1$ is H, $R_2$ is not OH.

X is H, alkyl of 1–6 carbon atoms, cyano, nitro, triflouromethyl, or halogen;

n is 2 or 3;

Y is a saturated, partially saturated or unsaturated 5–7 membered heterocycle containing a nitrogen, which may optionally contain a second heteroatom selected from the group consisting of —O—, —NH—, alkylamine of 1–6 carbon atoms, —N=, and $S(O)_m$;

m is 0–2;

or a pharmaceutically acceptable salt thereof.

Preferred compounds are those in which $R_1$ is selected from H, OH or the $C_1$-$C_{12}$ esters or alkyl ethers thereof, halogen;

$R_2$, $R_3$, $R_4$, $R_5$, and $R_6$ are independently selected from H, OH or the $C_1$-$C_{12}$ esters or alkyl ethers thereof, halogen, cyano, $C_1$-$C_6$ alkyl, or trihalomethyl, preferably trifluoromethyl, with the proviso that, when $R_1$ is H, $R_2$ is not OH;

X is selected from H, $C_1$-$C_6$ alkyl, cyano, nitro, triflouromethyl, halogen;

and Y is 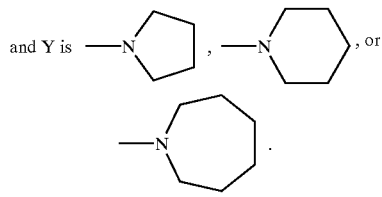

The preparation of the anti-estrogens of Formulas I and II and pharmaceutically acceptable salts of these compounds are disclosed in U.S. Pat. No. 5,998,402, which is hereby incorporated by reference.

Specifically preferred anti-estrogens of formulas I and II are shown in the Tables below.

TABLE 1

| Example No. | X | Q | Z |
|---|---|---|---|
| No. 1 | OBn | 4'-OEt | piperidine |
| No. 2 | OBn | H | azepane |
| No. 3 | OBn | 4'-OBn | piperidine |
| No. 4 | OBn | 4'-OBn | azepane |
| No. 5 | OBn | 4'-F | azepane |
| No. 6 | OBn | 4'-F | piperidine |
| No. 7 | OBn | 4'-Cl | piperidine |
| No. 8 | OBn | 3',4'-OCH$_2$O— | piperidine |
| No. 9 | OBn | 4'-O-iPr | piperidine |
| No. 10 | OBn | 4'-CH$_3$ | piperidine |
| No. 11 | OBn | 3'-OBn | piperidine |
| No. 12 | OBn | 3'-OBn | azepane |
| No. 13 | OBn | 4'-OBn, 3'-F | piperidine |
| No. 14 | OBn | 4'-OBn, 3'-F | azepane |
| No. 15 | OBn | 3'-OMe | piperidine |
| No. 16 | OBn | 4'-OCF$_3$ | piperidine |
| No. 17 | OBn | 4'-OBn | N-methylpiperazine |
| No. 18 | OBn | 3'-OMe | azepane |

TABLE 2

| Example No. | X | Q | Z |
|---|---|---|---|
| No. 19 | H | H | piperidine (6-ring N) |
| No. 20 | H | 4'-OH | piperidine (6-ring N) |
| No. 21 | OH | H | piperidine (6-ring N) |
| No. 22 | OMe | 4'-OH | piperidine (6-ring N) |
| No. 23 | OH | 4'-OMe | piperidine (6-ring N) |
| No. 24 | OMe | 4'-OMe | piperidine (6-ring N) |
| No. 25 | OMe | 4'-OMe | azepane (7-ring N) |
| No. 26 | OH | 4'-OEt | piperidine (6-ring N) |
| No. 27 | OH | 4'-OEt | azepane (7-ring N) |
| No. 28 | F | 4'-OH | piperidine (6-ring N) |

TABLE 2-continued

| Example No. | X | Q | Z |
|---|---|---|---|
| No. 29 | OH | H | azepane (7-ring N) |
| No. 30 | OH | 4'-OH | pyrrolidine (5-ring N) |
| No. 31 | OH | 4'-OH | piperidine (6-ring N) |
| No. 32 | OH | 4'-OH | azepane (7-ring N) |
| No. 33 | OH | 4'-OH | azocane (8-ring N) |
| No. 34 | OH | 4'-F | piperidine (6-ring N) |
| No. 35 | OH | 4'-F | azepane (7-ring N) |
| No. 36 | OH | 3'-OMe, 4'-OH | piperidine (6-ring N) |
| No. 37 | OH | 3',4'-OCH₂O— | piperidine (6-ring N) |
| No. 38 | OH | 4'-O-iPr | piperidine (6-ring N) |

TABLE 2-continued
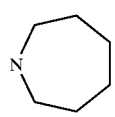
| Example No. | X | Q | Z |
|---|---|---|---|
| No. 39 | OH | 4'-O-iPr | 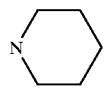 |
| No. 40 | OH | 4'-O—Cp | 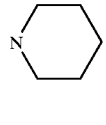 |
| No. 41 | OH | 4'-Cl | 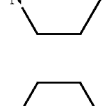 |
| No. 42 | OH | 2',4',-Dimethoxy | 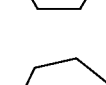 |
| No. 43 | OH | 3'-OH | 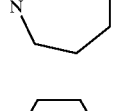 |
| No. 44 | OH | 3'-OH | 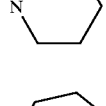 |
| No. 45 | OH | 4'-OH, 3'-F | 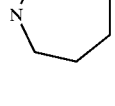 |
| No. 46 | OH | 4'-OH, 3'-F | 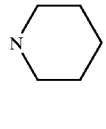 |
| No. 47 | OH | 3'-OMe | 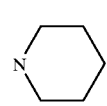 |
TABLE 2-continued
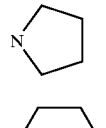
| Example No. | X | Q | Z |
|---|---|---|---|
| No. 48 | OH | 4'-OCF$_3$ | 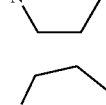 |
TABLE 3
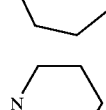
| Example No. | X | Q | Z |
|---|---|---|---|
| No. 49 | Cl | H | 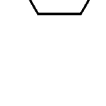 |
| No. 50 | Cl | H | |
| No. 51 | Cl | H | |
| No. 52 | Cl | CH$_3$ | |

TABLE 3-continued

| Example No. | X | Q | Z |
|---|---|---|---|
| No. 53 | Et | H | piperidin-1-yl |
| No. 54 | CN | H | piperidin-1-yl |
| No. 55 | CN | H | azepan-1-yl |

TABLE 4

| Example No. | R | Z |
|---|---|---|
| No. 56 | Et | azepan-1-yl |
| No. 57 | t-Bu | azepan-1-yl |

TABLE 4-continued

| Example No. | R | Z |
|---|---|---|
| No. 58 | t-Bu | piperidin-1-yl |

Particularly preferred anti-estrogens of Formulas I or II are those of Examples 31 (2-(4-hydroxy-phenyl)-3-methyl-1-[4-(2-piperdin-1-yl-ethoxy)-benzyl-1H-indol-5-ol) and 32(1-[4-(2-azepan-1-yl-ethoxy)-benzyl]-2-(4-hydroxy-phenyl)-3-methyl-1H-indo the tables above.

When applicable, pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when the rapamycin or antiestrogen contains a suitable basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when the rapamycin or antiestrogen contains a suitable acidic moiety.

As used in accordance with this invention, the term "providing," with respect to providing a compound or substance covered by this invention, means either directly administering such a compound or substance, or administering a prodrug, derivative, or analog which will form the equivalent amount of the compound or substance within the body.

The ability of the combination of the rapamycins and antiestrogens of this invention to treat or inhibit estrogen receptor positive carcinoma was confirmed in three standard pharmacological test procedures which measured the ability of the rapamycin antiestrogen combination to inhibit the growth of MCF-7 breast cancer cells and BG-1 ovarian cancer cells, as representative estrogen receptor positive carcinoma. In these test procedures, rapamycin 42-ester with 3-hydroxy-2-(hydroxymethyl)-2-methylpropionic acid was used as a representative rapamycin, and 2-(4-hydroxy-phenyl)-3-methyl-1-[4-(2-piperdin-1-yl-ethoxy)-benzyl-1H-indol-5-ol, raloxifene, and 4-hydroxytamoxifen were used as representative antiestrogens. The following briefly describes the procedures used, and results obtained.

MCF-7 human breast cancer cells were maintained at 37° C. in a humidified atmosphere of 5% $CO_2$ and 95% air in IMEM medium supplemented with 10% fetal bovine serum. BG-1 human ovarian cancer cells were maintained at 37° C. in a humidified atmosphere of 5% $CO_2$ and 95% air in IMEM medium supplemented with 10% fetal bovine serum, 2 ug/ml insulin, and 1% non-essential amino acids. One day before the experiment, cells were plated in 96-well plates at a cell density of 2,500 cells/well in IMEM medium supplemented with 10% fetal bovine serum. The next day, cells were treated with various concentrations of antiestrogen and rapamycin 42-ester with 3-hydroxy-2-(hydroxymethyl)-2-methylpropionic acid (referred to as CCI-779 in the tables below). Five or six-days later, cell growth was monitored. MTT solution (20 ul) (0.5 mg/ml) was added to each well and cells were incubated for an additional 4 h. The solution was then removed and 150 ul of DMSO added. The intensity of dark blue color corresponding to number of cells was read at 540 nM with an automated plate reader.

The following tables summarize the results obtained; 2-(4-hydroxy-phenyl)-3-methyl-1-[4-(2-piperdin-1-yl-ethoxy)-benzyl-1H-indol-5-ol is referred to as ERA-923 in the tables below.

TABLE A

Effect of CCI-779 and ERA-923 on MCF-7 Cells
(Percent inhibition)

| | CCI-779 | | | | | |
|---|---|---|---|---|---|---|
| ERA-923 | 0 nM | 5 nM | 10 nM | 50 nM | 100 nM | 200 nM | 400 nM |
| 0 nM | 0 | −13.25 | −1.54 | 26.68 | 37.93 | 34.99 | 39.43 |
| 0.25 nM | 9 | 13.92 | 40.37 | 77.67 | 84.23 | 84.64 | 87.24 |
| 0.5 nM | 7.59 | 47.78 | 70.46 | 87.07 | 90.76 | 89.93 | 87.42 |
| 1 nM | 37.56 | 63.14 | 80.48 | 90.95 | 91.47 | 91.04 | 92.6 |
| 2 nM | 54.65 | 68.96 | 78.89 | 90.89 | 90.83 | 92.19 | 92.71 |
| 3 nM | 59.39 | 75.41 | 84.98 | 90.71 | 92.55 | 92.57 | 94.17 |
| 4 nM | 60.04 | 71.03 | 83.33 | 92.48 | 91.72 | 93.81 | 95.77 |
| 5 nM | 61.12 | 84.72 | 87.19 | 93.6 | 93.99 | 95.41 | 95.34 |

TABLE B

Effect of CCI-779 and 4-Hydroxytamoxifen on MCF-7 Cells
(Percent Inhibition)

| | CCI-779 | | | | | |
|---|---|---|---|---|---|---|
| TAM | 0 nM | 5 nM | 10 nM | 50 nM | 100 nM | 200 nM | 400 nM |
| 0 nM | 0 | −16.48 | 1.47 | 14.99 | 24.63 | 25.25 | 33.96 |
| 5 nM | 20.44 | 33.31 | 44.98 | 73.78 | 73.72 | 74.18 | 75.37 |
| 10 nM | 22.75 | 44.37 | 51.72 | 75.38 | 75.07 | 74.9 | 77.81 |
| 20 nM | 39.85 | 50.36 | 57.31 | 74.27 | 73.72 | 74.37 | 76.75 |
| 30 nM | 41.46 | 48.39 | 58.97 | 70.8 | 71.72 | 73.51 | 76.15 |
| 40 nM | 39.09 | 47.82 | 51.27 | 71.21 | 70.35 | 73.27 | 75.77 |
| 50 nM | 47.19 | 51.47 | 50.99 | 70.38 | 69.74 | 71.2 | 73.77 |
| 100 nM | 36.99 | 52.68 | 54.2 | 69.37 | 65.81 | 68.84 | 73.74 |

TABLE C

Effect of CCI-779 and Raloxifene on MCF-7 Cells
(Percent Inhibition)

| | CCI-779 | | | | | |
|---|---|---|---|---|---|---|
| RAL | 0 nM | 5 nM | 10 nM | 50 nM | 100 nM | 200 nM | 400 nM |
| 0 nM | 0 | −13.83 | −3.3 | 35.34 | 38.06 | 38.08 | 39.81 |
| 0.25 nM | 1.4 | −13.31 | 11.5 | 50.51 | 56.51 | 58.87 | 64.17 |
| 0.5 nM | −5.17 | −4.35 | 28.95 | 68.66 | 68.18 | 75.15 | 79.38 |
| 1 nM | 17.3 | 37.14 | 50.4 | 83.52 | 83.26 | 88.04 | 88.85 |
| 2 nM | 36.78 | 45.73 | 65.83 | 87.68 | 88.55 | 91.79 | 93.91 |
| 3 nM | 42.4 | 53.84 | 70.14 | 87.8 | 89.19 | 89.53 | 92.86 |
| 4 nM | 50.49 | 60.19 | 75.74 | 89.19 | 91.04 | 91.7 | 93.26 |
| 5 nM | 50.5 | 69.24 | 78.18 | 89.73 | 90.49 | 93.05 | 95.09 |

TABLE D

Effect of ERA-923 (Alone) on MCF-7 Cells
(Percent Inhibition)

| | ERA-923 | | | | | |
|---|---|---|---|---|---|---|
| ERA-923 | 0 nM | 0.25 nM | 0.5 nM | 1 nM | 2 nM | 3 nM | 4 nM |
| 0 nM | 0 | 6.69 | 8.17 | 42.1 | 67.81 | 52.23 | 74.49 |
| 0.25 nM | −0.78 | 35.93 | 53.61 | 66.83 | 74.73 | 75.24 | 79.39 |
| 0.5 nM | 26.09 | 56.79 | 63.08 | 75.09 | 75.08 | 76.06 | 80.92 |
| 1 nM | 54.91 | 64.27 | 68.58 | 74.24 | 75.36 | 77.68 | 77.2 |
| 2 nM | 71.82 | 76.33 | 73.71 | 74.07 | 75.03 | 76.67 | 78.2 |
| 3 nM | 87.65 | 78.99 | 81.21 | 76.56 | 78.5 | 81.51 | 79.28 |
| 4 nM | 78.72 | 78.39 | 79.57 | 80.45 | 81.23 | 83.2 | 83.28 |
| 5 nM | 79.25 | 79.68 | 81.43 | 82.97 | 82.02 | 82.87 | 85.92 |

TABLE E

Effect of CCI-779 (Alone) on MCF-7 Cells
(Percent Inhibition)

| | CCI-779 | | | | | |
|---|---|---|---|---|---|---|
| CCI-779 | 0 nM | 5 nM | 10 nM | 50 nM | 100 nM | 200 nM | 400 nM |
| 0 nM | 0 | 0.59 | 4.91 | 36.55 | 42.35 | 45.87 | 55.78 |
| 5 nM | −4.19 | 13.25 | 18.78 | 48.28 | 54.2 | 51.41 | 61.12 |
| 10 nM | 10.25 | 18.61 | 23.5 | 46.91 | 52.94 | 57.1 | 61.15 |
| 50 nM | 49.79 | 49.24 | 51.18 | 50.31 | 50.96 | 57.24 | 60.02 |
| 100 nM | 46.83 | 50.99 | 54.81 | 54.62 | 55.02 | 58.97 | 61.97 |
| 200 nM | 53.45 | 58.07 | 62.43 | 57.54 | 62.49 | 65.48 | 66.3 |
| 400 nM | 55.32 | 64.09 | 65.21 | 60.17 | 66.75 | 66.84 | 69.68 |

TABLE F

Effect of 4-Hydroxytamoxifen (Alone) on MCF-7 Cells
(Percent Inhibition)

| | TAM | | | | | |
|---|---|---|---|---|---|---|
| TAM | 0 nM | 5 nM | 10 nM | 50 nM | 100 nM | 200 nM | 400 nM |
| 0 nM | 0 | 12.73 | 27.87 | 39.46 | 46.41 | 45.75 | 48.85 |
| 5 nM | 25.02 | 37.12 | 47.71 | 48.51 | 52.37 | 54.54 | 52.28 |
| 10 nM | 37.37 | 49.04 | 47.11 | 51.71 | 50.34 | 51.06 | 58.29 |
| 20 nM | 44.9 | 50.12 | 45.86 | 46.36 | 47.64 | 52 | 56.61 |
| 30 nM | 42.42 | 50.39 | 47.6 | 42.54 | 48.22 | 49.75 | 57.28 |
| 40 nM | 46.46 | 54.19 | 53.22 | 48.3 | 51.79 | 59.13 | 59.68 |

TABLE F-continued

Effect of 4-Hydroxytamoxifen (Alone) on MCF-7 Cells
(Percent Inhibition)

| TAM | TAM 0 nM | 5 nM | 10 nM | 50 nM | 100 nM | 200 nM | 400 nM |
|---|---|---|---|---|---|---|---|
| 50 nM | 45.78 | 53.75 | 56.54 | 50.98 | 55.29 | 59.05 | 67.28 |
| 100 nM | 49.99 | 59.23 | 58.11 | 58.57 | 61.34 | 61.13 | 64.92 |

TABLE G

Effect of CCI-779 and ERA-923 on BG-1 Cells
(Percent Inhibition)

| ERA-923 | CCI-779 0 nM | 5 nM | 10 nM | 50 nM | 100 nM | 200 nM | 400 nM |
|---|---|---|---|---|---|---|---|
| 0 nM | 0 | 19.98 | 22.68 | 49.76 | 58.79 | 55.65 | 61.94 |
| 0.25 nM | 14.72 | 59.39 | 54.18 | 57.92 | 69.12 | 73.33 | 77.85 |
| 0.5 nM | 24.14 | 66.01 | 44.73 | 73.29 | 82.21 | 84.25 | 88.45 |
| 1 nM | 48.93 | 74.8 | 65.78 | 85.61 | 94.05 | 90.99 | 91.67 |
| 2 nM | 57.19 | 92.93 | 82.02 | 85.96 | 90.91 | 90.31 | 91.24 |
| 3 nM | 72.54 | 94.97 | 88.57 | 90.2 | 93.96 | 93.91 | 92 |
| 4 nM | 80.34 | 92.13 | 81.74 | 90.97 | 91.56 | 93.3 | 94.85 |
| 5 nM | 75.94 | 91.99 | 85.03 | 86.85 | 94.3 | 95.78 | 95.59 |

TABLE H

Effect of CCI-779 and 4-Hydroxytamoxifen on BG-1 Cells
(Percent Inhibition)

| TAM | CCI-779 0 nM | 5 nM | 10 nM | 50 nM | 100 nM | 200 nM | 400 nM |
|---|---|---|---|---|---|---|---|
| 0 nM | 0 | 21.38 | 24.93 | 56.31 | 56.37 | 60.68 | 64.93 |
| 5 nM | 23.99 | 44.37 | 41.86 | 69.61 | 66.63 | 71.14 | 79.24 |

TABLE H-continued

Effect of CCI-779 and 4-Hydroxytamoxifen on BG-1 Cells
(Percent Inhibition)

| TAM | CCI-779 0 nM | 5 nM | 10 nM | 50 nM | 100 nM | 200 nM | 400 nM |
|---|---|---|---|---|---|---|---|
| 10 nM | 21.39 | 55.09 | 59.32 | 68.95 | 65.73 | 72.51 | 75.3 |
| 20 nM | 35.05 | 56.7 | 60.76 | 73.68 | 75.57 | 75.71 | 78.67 |
| 30 nM | 36.43 | 52.12 | 52.53 | 73.61 | 71.76 | 73.18 | 79.34 |
| 40 nM | 39.51 | 54.51 | 54.16 | 72.6 | 74.87 | 75.9 | 75.12 |
| 50 nM | 47.73 | 53.87 | 61.25 | 75.35 | 75.54 | 80.41 | 83 |
| 100 nM | 50 | 63.03 | 66.39 | 76.05 | 76.66 | 82.41 | 83.99 |

TABLE I

Effect of CCI-779 and Raloxifene on BG-1 Cells
(Percent Inhibition)

| RAL | CCI-779 0 nM | 5 nM | 10 nM | 50 nM | 100 nM | 200 nM | 400 nM |
|---|---|---|---|---|---|---|---|
| 0 nM | 0 | 8.26 | 12.46 | 37.69 | 42.15 | 48.36 | 53.03 |
| 0.25 nM | 0.74 | 3.26 | 18.41 | 41.02 | 44.63 | 43.67 | 49.32 |
| 0.5 nM | −3.32 | 12.13 | 25.71 | 38.32 | 42.81 | 50.22 | 51.64 |
| 1 nM | 7.79 | 21.5 | 33.74 | 47.59 | 52.48 | 56.95 | 61.41 |
| 2 nM | 9.85 | 29.22 | 40.95 | 61.14 | 60.83 | 62.95 | 65.37 |
| 3 nM | 11.5 | 35.79 | 44.63 | 63.98 | 64.96 | 68.01 | 73.02 |
| 4 nM | 14.49 | 40.85 | 48.93 | 64.55 | 67.44 | 72.09 | 73.88 |
| 5 nM | 14.04 | 49.46 | 48.45 | 74.98 | 72 | 76.32 | 76.51 |

An analysis was conducted using a 3-D graphing shareware, MacSynergy II, developed by Prichard and his colleagues (Prichard and Shipman, 1990: 1992) to determine whether the rapamycin plus antiestrogen combination synergistically inhibited estrogen receptor positive carcinoma. Briefly, theoretical additive interactions were calculated from the dose-response curves of each individual drug based on Bliss independence model. The calculated additive surface was then subtracted from the experimental surface to obtain a synergy surface representing % inhibition above the calculated additive value-synergy index. Any peak above the 0% plane suggests synergy. Likewise, any peak below the 0% plane is indicative of antagonism. The results are summarized in the table below for the combinations of rapamycin 42-ester with 3-hydroxy-2-(hydroxymethyl)-2-methylpropionic acid plus the antiestrogens shown in the lefthand column.

| Compound | MCF-7 Synergy ($\mu M^2$ %) | Antagonsim ($\mu M^2$ %) | BG-1 Synergy ($\mu M^2$ %) | Antagonism ($\mu M^2$ %) |
|---|---|---|---|---|
| ERA-923 | 138.0 | 0.0 | 25.9 | 0.0 |
| 4-OH Tamoxifen | 77.00 | 0.0 | 0.3 | 0.0 |
| Raloxifene | 113.0 | 0.0 | 40.3 | −1.8 |

The results obtained in these standard pharmacological test procedures showed that the combination of a rapamycin and an antiestrogen synergistically inhibited the growth of estrogen receptor positive carcinoma. For example, the results showed that treatment of MCF-7 breast cancer cells with a combination of ERA-923 and CCI-779, caused a definite synergistic enhancement of growth inhibition. The growth-inhibitory effect of ERA-923 in the presence of non-inhibitory concentrations of CCI-779 was increased by approximately 10-fold as estimated by the $IC_{50}$, whereas growth inhibition by CCI-779 in the presence of non-inhibitory concentrations of ERA-923 was increased approximately 40-fold. As shown in Table A, synergy was more pronounced at low concentrations of ERA-923 (0.25 nM-1 nM) in combination with high concentrations of CCI-779 (300–400 nM). The highest degree of synergy of observed was about 60% above additive value.

Similar results were shown with the antiestrogens raloxifene and 4-hydroxytamoxifen, in combination with CCI-779. Both raloxifene and 4-hydroxytamoxifen demonstrated synergistic inhibition in the presence of CCI-779. Synergistic inhibition of MCF-7 cells with 4-hydroxytamoxifen in combination with CCI-779 having optimal concentrations ranging from 5 to 20 nM (4-hydroxytamoxifen) and 5 to 400 nM (CCI-779) (Table B). The combination of raloxifene and CCI-779 was also synergistic at a broad range of concentrations of either drug ranging from 0.25–5.0 nM raloxifene and 5.0–400 nM CCI-779 (Table C)

Synergistic inhibition was also demonstrated in estrogen-dependent BG-1 ovarian cancer cells when antiestrogens except 4-hydroxytamoxifen were combined with a rapamycin, such as CCI-779 (Table G, H, I). The failure of 4-hydroxytamoxifen and CCI-779 to demonstrate synergistic inhibition in BG-1 cells is probably associated with 4-hydroxytamoxifen's partial agonist activity in ovary.

In the third standard pharmacological test procedure, mice implanted with MCF-7 tumors were treated with a combination of ERA-923 and CCI-779. The following briefly summarizes the procedure used and results obtained. ERA-923 was dissolved in 1% Tween 80 and 0.9% NaCl Injection USP. Drug was aliquoted into daily doses using 10.0 ml glass bottles and frozen at −20° C. until needed. CCI-779 was made fresh using a 5% ETOH, 4.9% Phosal and 0.1% Tween 80 in Sterile Water. 0.2 ml of each drug was given orally starting the day after tumor implantation. ERA 923 was given daily for the duration of the experiment and CCI-779 was given every other day for the first 10 days. The control vehicles were given on the same regime as the drugs. MCF7 cells were cultured in IMEM containing 5% Fetal Bovine Serum with passages varying from 2–20. After trypsinization tumors were resuspended in IMEM with 2% Serum at a 1:1 ratio with Matrigel. 10 million cells were injected subcutaneously into the mammary tissue of each mouse using a 1.0 ml tuberculin syringe with a 23 ¾ gauge needle. Five to six week old female ovariectomized athymic nu/nu mice (Charles River Labs: Wilmington, Mass.) weighing from 20.0–23.0 g were used. The animals were housed 5 to a cage in a Microisolator Open Rack System (Lab Products: Maywood, N.J.). Each mouse received a 17β-Estradiol pellet (0.72 mg/pellet-60 day release). The pellets were injected with a 10 gauge trochar into the lateral side of the neck between the ear and the shoulder 1–2 weeks prior to tumor injection. Control groups were 15 mice/vehicle whereas the drug groups were 10 mice/drug. Tumors were measured weekly by means of solar calipers (Cole-Parmer Instuments: Vernon Hills, Ill.) and tumor weights were estimated from tumor diameters by the following formula:

Tumor weight (mg)=tumor length (mm)×tumor width $(mm)^2/2$.

Mice were euthanized 36 days after tumor injection by $CO_2$ inhalation. The following summarizes the results that were obtained. Nude mice bearing MCF-7 tumors were given ERA-923, CCI-779 or the combination of both drugs. Under these conditions, ERA-923 or CCI-779 had a partial effect (approximately 35% inhibition of growth; growth inhibition=experimental value−200 (baseline)/control value−200). However, the combination of the drugs inhibited tumor growth approximately 85%. No signs of toxicity were observed with this drug combination. The results are summarized in the table below.

| Effect of combination treatment with CCI-779 and ERA-923 on the growth of MCF-7 breast carcinoma in nude mice[1] | | | | |
|---|---|---|---|---|
| Days after tumor implantation | Control treatment[2] | 5 mg/kg CCI-779 (PO; q2d days 1–9)[3] | 20 mg/kg ERA-923 (PO qd days 1–35)[4] | 5 mg/kg CCI-779 plus 20 mg/kg ERA-923[5] |
| 14 | 495 ± 46 | 260 ± 18* | 480 ± 91 | 290 ± 22−/* |
| 21 | 789 ± 83 | 485 ± 53* | 679 ± 127 | 331 ± 34*/* |
| 28 | 1111 ± 134 | 704 ± 63 | 842 ± 163 | 398 ± 33*/* |
| 36 | 1425 ± 179 | 1123 ± 134 | 993 ± 197* | 498 ± 88*/* |

[1]Ovariectomized nude mice were given 0.72 mg 60-day slow release 17 β-estradiol pellets one week prior to implantation with $1 \times 10^7$ MCF-7 tumor cells near the animal's mammary glands. One day after tumor implantation, oral drug therapy (PO) was given as indicated. Tumor size was measured on the days specified according to previously stated methods (see Discafani et al., 1999. Biochem Pharmacol. 57: 917–925).
[2]Control treatment is the combined effect of animals treated with vehicle for CCI-779 (phosal), vehicle for ERA-923 (tween), or vehicle for both drugs. The average tumor sizes of each control group did not significantly vary from each other and therefore were pooled. Values are mean ± standard error. Statistical analysis was done using log transformation of the data followed by ANOVA; pair-wise comparisons were done. The single asterisks refers to statistical significance at $p < 0.05$ compared to the control group. The double asterisk (*/*) or −/* refers to statistical significance, or lack therof, in a pair wise comparison with CCI-779 or ERA-923 given alone. The values in the CCI-779 plus ERA-923 group were statistically different compared to control at the $p < 0.001$ level.
[3]CCI-779 in phosal was given orally every other day beginning on day 1 and terminating on day 9.
[4]ERA-923 in tween was given orally every day beginning on day 1.
[5]Drugs were given as two separate doses. Dosing was done on the days specified in the groups where the drug was given alone.

Based on the results obtained in the standard pharmacological test procedure described above, the combination of a rapamycin and an antiestrogen are useful in treating or inhibiting estrogen receptor positive carcinoma, particularly estrogen receptor positive breast or ovary carcinima.

It is understood that the effective dosage of the combination of a rapamycin and antiestrogen may vary depending upon the particular compound utilized, the mode of administration, the condition, and severity thereof, of the condition being treated, as well as the various physical factors related to the individual being treated. It is projected that a combination of CCI-779 (as a representative rapamycin) and ERA-923 (as a representative antiestrogen) will be administered once weekly at a projected dosage of 5–500 mg CCI-779 (with a preferred dosgae of 50–200 mg) and 2–500 mg ERA-923 (with a preferred dosage of 25–100 mg). Initial dosages of other rapamycins and antiestrogens can be obtained by comparing the relative potencies with CCI-779 and ERA-923.

As used in this invention, the combination regimen can be given simultaneously or can be given in a staggered regimen, with the rapamycin being given at a different time during the course of chemotherapy than the antiestrogen. This time differential may range from several minutes, hours, days, weeks, or longer between administration of the two agents. Therefore, the term combination does not necessarily mean administered at the same time or as a unitary dose, but that each of the components are administered furing a desired treatment period. For example, in the combination of CCI-779 and ERA-923, it is anticipated that the CCI-779 will be administered parenterally, and the ERA-923 will be administered orally. The combination can be administered daily, weekly, or even once monthly. As typical for chemotherapeutic regimens, a course of chemotherapy may be repeated several weeks later, and may follow the same timeframe for administration of the two agents, or may be modified based on patient response.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. It is more preferred that poloxamer 188 is used as the surface modifying agent. Oral formulations herein may utilize standard delay or time release formulations to alter the absorption of the active compound(s). Preferred oral formulations of rapamycins are disclosed in U.S. Pat. Nos. 5,559,121; 5,536,729; 5,989,591; and 5,985,325, which are hereby incorporated by reference.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Preferred parenteral formulations for administering a rapamycin are disclosed in U.S. Pat. Nos. 5,530,006; 5,516,770; and 5,616, 588, which are hereby incorporated by reference.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

What is claimed is:

1. A method of treating or inhibiting an estrogen receptor positive carcinoma in a mammal in need thereof, which comprises providing said mammal with synergistically effective amounts of a rapamycin and an antiestrogen in combination.

2. The method according to claim 1, wherein the rapamycin is rapamycin.

3. The method according to claim 1, wherein the rapamycin is a ester, ether, oxime, hydrazone, or hydroxylamine of rapamycini.

4. The method according to claim 3, wherein the rapamycin is a 42-ester or 42-ether of rapamycin.

5. The method according to claim 4, wherein the rapamycin is rapamycin 42-ester with 3-hydroxy-2-(hydroxymethyl)-2-methylpropionic acid.

6. The method according to claim 4, wherein the rapamycin is 42-O-(2-hydroxy)ethyl rapamycin.

7. The method according to claim 1, wherein the antiestrogen is tamoxifen, 4-hydroxytamoxifen, or clomiphene.

8. The method according to claim 1, wherein the antiestrogen is a non-uterotophic estrogen.

9. The method according to claim 8, wherein the non-uterotrophic antiestrogen is selected from the group consisting of raloxifene, droloxifene, idoxifine, nafoxidine, toremifene, TAT-59, levomeloxifene, LY-353381, CP-336156, MDL-103323, EM-800, and ICI-182,780.

10. The method according to claim 8, wherein the non-uterotrophic antiestrogen is a compound of formulas I or II having the structures

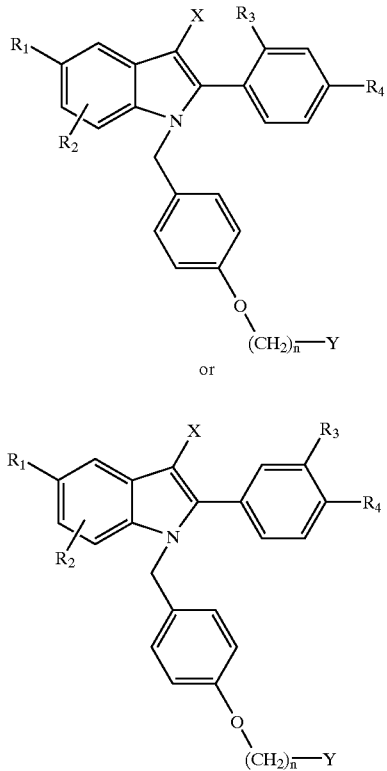

wherein:
- $R_1$ is H, OH, carboalkoxy of 2–12 carbon atoms, alkoxy of 1–12 carbon atoms, halogen or mono- or polyfluoroalkoxy of 1–12 carbon atoms;
- $R_2$ is H, OH, carboalkoxy of 2–12 carbon atoms, alkoxy of 1–12 carbon atoms, halogen, mono- or polyfluoroalkoxy of 1–12 carbon atoms, cyano, alkyl of 1–6 carbon atoms, or trifluoromethyl, with the proviso that, when $R_1$ is H, $R_2$ is not OH.
- $R_3$ and $R_4$ are each, independently, H, OH, carboalkoxy of 2–12 carbon atoms, alkoxy of 1–12 carbon atoms, halogen, mono- or poly-fluoroalkoxy of 1–12 carbon atoms, or cyano, with the proviso that, when $R_1$ is H, $R_2$ is not OH.
- X is H, alkyl of 1–6 carbon atoms, cyano, nitro, triflouromethyl, or halogen;
- n is 2 or 3;
- Y is a saturated, partially saturated or unsaturated 5–7 membered heterocycle containing a nitrogen, which may optionally contain a second heteroatom selected from the group consisting of —O—, —NH—, alkylamine of 1–6 carbon atoms, —N=, and $S(O)_m$;
- m is 0–2 or a pharmaceutically acceptable salt thereof.

11. The method according to claim 10, wherein the antiestrogen is (2-(4-hydroxy-phenyl)-3-methyl-1-[4-(2-piperdin-1-yl-ethoxy)-benzyl-1H-indol-5-ol or a pharmaceutically acceptable salt thereof.

12. The method according to claim 10, wherein the antiestrogen is (1-[4-(2-azepan-1-yl-ethoxy)-benzyl]-2-(4-hydroxy-phenyl)-3-methyl-1H-indol-5-ol) or a pharmaceutically acceptable salt thereof.

13. The method according to claim 1, wherein the estrogen receptor positive carcinioma is of the breast or ovary.

14. The method according to claim 1, wherein the rapamycin is rapamycin 42-ester with 3-hydroxy-2-(hydroxymethyl)-2-methylpropionic acid, and the antiestrogen is (2-(4-hydroxy-phenyl)-3-methyl-1-[4-(2-piperdin-1-yl-ethoxy)-benzyl-1H-indol-5-ol) or a pharmaceutically acceptable salt thereof.

15. A method of treating or inhibiting estrogen receptor positive carcinoma of the breast in a mammal in need thereof, which comprises providing to said mammal synergistically effective amounts, of a combination of rapamycin 42-ester with 3-hydroxy-2-(hydroxymethyl)-2-methylpropionic acid and (2-(4-hydroxy-phenyl)-3-methyl-1-[4-(2-piperdin-1-yl-ethoxy)-benzyl-1H-indol-5-ol or a pharmaceutically acceptable salt thereof.

16. A method of treating or inhibiting estrogen receptor positive carcinoma of the ovary in a mammal in need thereof, which comprises providing to said mammal synergistically effective amounts of a combination of rapamycin 42-ester with 3-hydroxy-2-(hydroxymethyl)-2-methylpropionic acid and (2-(4-hydroxy-phenyl)-3-methyl-1-[4-(2-piperdin-1-yl-ethoxy)-benzyl-1H-indol-5-ol) or a pharmaceutically acceptable salt thereof.

* * * * *